United States Patent [19]

Fukuda

[11] Patent Number: 5,174,755
[45] Date of Patent: Dec. 29, 1992

[54] DENTAL IMPLANT

[75] Inventor: Hiroshi Fukuda, Tokyo, Japan

[73] Assignee: Olympus Optical Co., Ltd., Tokyo, Japan

[21] Appl. No.: 778,250

[22] Filed: Oct. 17, 1991

[30] Foreign Application Priority Data

Oct. 25, 1990 [JP] Japan .................................. 2-285723

[51] Int. Cl.⁵ ............................................. A61C 8/00
[52] U.S. Cl. ..................................... 433/173; 433/169
[58] Field of Search ............... 433/169, 173, 174, 175, 433/176; 606/78; 623/36, 55

[56] References Cited

U.S. PATENT DOCUMENTS 4,468,201 8/1984 Fukuyo ................................ 433/176
4,713,006 12/1987 Hakamatsuka et al. ........... 433/201.1
5,026,280 6/1991 Durr et al. .......................... 433/173

FOREIGN PATENT DOCUMENTS 58-116353 7/1983 Japan .
62-38148  2/1987 Japan .
63-9451   1/1988 Japan .
63-103616 7/1988 Japan .

OTHER PUBLICATIONS

"IME (Intramobile Element)", Quintessence of Dental Technology, vol. 15, May 1990, pp. 29-31.

Primary Examiner—Cary E. O'Connor
Attorney, Agent, or Firm—Frishauf, Holtz, Goodman & Woodward

[57] ABSTRACT

A dental implant comprising an artificial root which is embedded in a jaw bone and a post to which an artificial tooth is attached, wherein a stress absorbing member made of a super elastic material is provided in at least a part of the implant between the artificial root and the post. Preferably, a stress absorbing system consisting of a super elastic material member and a polymeric material member is employed.

15 Claims, 6 Drawing Sheets

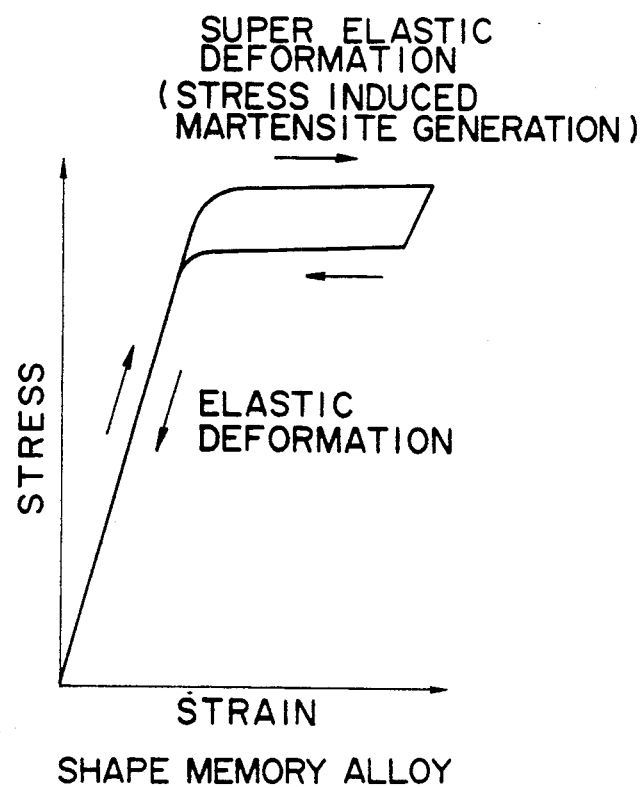
F I G. 1
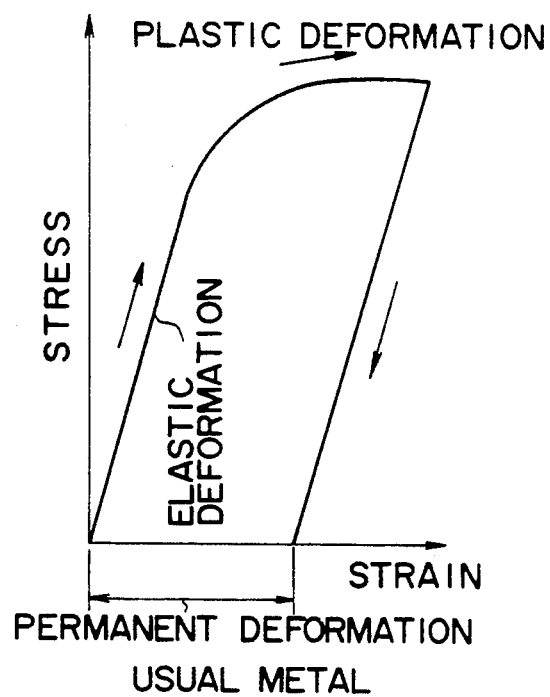
F I G. 2

DENTAL IMPLANT

BACKGROUND OF THE INVENTION

1. Field of the Invention

This invention relates to an improved dental implant used in the field of dental therapy.

2. Description of the Related Art

Recently, extensive studies are being made on the dental implant technology as a prosthesis means for the treatment of dental fall off and damages. The purpose of this technology is to embed a dental implant having the functions equal to those of the original tooth in the position from which the tooth is fallen off or extracted because of the damage.

Conventionally, dental implants, made of titanium or titanium alloy, or single crystalline alumina have been widely employed. For the purpose of enhancing the affinity with bone it has been proposed in the art that, titanium or titanium alloy implants whose surfaces are to be in contact with the bone be covered with hydroxyapatite (HAP) or calcium phospate (TCP).

Most of these conventional dental implants, however, have no function corresponding to that of the periodontal membrane of natural tooth, especially the function of shock absorber. The dental implant which lacks the shock absorbing function, for example, an implant shown in FIG. 12, has been known. The implant of FIG. 12 comprises an implant body 3a made of titanium which is embedded in jaw bone, a gingiva-penetrating member 4 made of titanium which is engaged with an upper end portion of the implant body 3a, a post core 10 made of titanium which is screwed through the gingiva-penetrating member 4 into a post core fixing hole provided in the implant body 3a, an artificial tooth 8 fixed on the post core 10 using a securing pin 11, and a filler member 12 buried in a space formed above the securing pin 11. Such a dental implant allow direct transmission of the occlusal force to jaw bone 1, which gives a great stress to the jaw bone in case of excess occlusal force applied, resulting in damage to the jaw bone.

Unexamined Japanese Patent Publication 58-116353 also discloses a dental implant provided with a shock absorbing member between an inner crown and an outer crown.

In addition, Unexamined Japanese Patent Publication 62-38148 (corresponding to U.S. Pat. No. 4,713,006) discloses a dental implant in which a shock absorbing member made of polymeric material such as silicone rubber, polyoxymethylene (POM) and the like is provided between the implant body and the post core in order to absorb and reduce the impact force loaded on the tooth crown.

FIG. 13 shows one example of such a dental implant having a shock absorbing member. The dental implant of FIG. 13 has an implant body 3a embedded in jaw bone 1. A gingiva-penetrating member 4 of cylindrical shape is engaged with an upper end portion of the implant body 3a, and fixed by screwing a polymeric material member 5b into the implant body 3a through the gingiva-penetrating member 4. On a central portion of an upper end of the gingiva-penetrating member 4, there is provided a threaded hole into which a securing pin 11 is screwed, in order to fix an artificial tooth 8 by screwing the pin 11 into the threaded hole. The artificial tooth 8 has a space on the securing pin 11, in which space a filler member 12 is buried.

The dental implants having the shock absorbing system described above, however, have following problems.

The first problem is that the excessive movement of the crown due to a great deformation of shock absorbing member made of the polymeric material results in a poor occlusal force.

The second problem is that periodic replacement of the shock absorbing member is required in order to prevent degradation or destruction of the polymeric material.

For avoiding the occurrence of the first and the second problems described above, there has been proposed a dental implant wherein, as shown in FIG. 14, disk-shaped shock absorbing member 5c made of polymeric material is employed in order to prevent deterioration of the shock absorbing member. In FIG. 14, the shock absorbing disk 5c made of polymeric material such as polyoxymethylene is disposed on the gingiva-penetrating member 4 which is screwed into the implant body 3a to be fixed. Both the gingiva-penetrating member 4 and the implant body 3a are made of titanium. Then, artificial tooth 8 is fixed on the shock absorbing member 5c by screwing the securing pin 11 into the gingiva-penetrating member 4 through the disk 5c. As a result, the shock absorbing disk 5c is sandwiched between the gingiva-penetrating member 4 and the artificial tooth 8 to be fixed.

The dental implant of FIG. 14 can reduce the stress imposed on the shock absorbing disk because occlusal force imposed on the artificial tooth 8 is mainly assigned to the securing pin 11.

However, the dental implant shown in FIG. 14 has another problem in that the stress from occlusal force is focused on the neck of the securing pin 11, fixing the shock absorbing disk 5c so as to give residual strain to the securing pin 11, thereby resulting in deviation of the occlusal position.

SUMMARY OF THE INVENTION

The problems mentioned above are solved by the present invention, which has been achieved in order to provide a dental implant which enables a sufficient occlusal force to be obtained while preventing excessive stress from being imposed on a jaw bone, without need for replacement of the shock absorbing member, by means of improvement of the shock absorbing system.

For the purpose of solving the problems mentioned above, the present invention employs a shock absorbing system which consists of either a super elastic material member or a combination of a super elastic material member and a polymeric material member.

In the case of employing a shock absorbing system consisting of a polymeric material member and a super elastic material member, the dental implant according to the present invention is so designed that the super elastic material member directly connects the implant body and the post core without interposition of the polymeric material member. The polymeric material member is provided in such a manner, for example, that the space among the super elastic material member, the gingiva penetrating member and the post core is filled with the polymeric material member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 shows a curve of stress vs. strain representing the super elasticity of a shape memory alloy.

FIG. 2 shows a curve of stress vs. strain obtained when using an usual metal material.

DETAILED DESCRIPTION OF THE PREFERRED EMBODIMENTS

Figure 3:
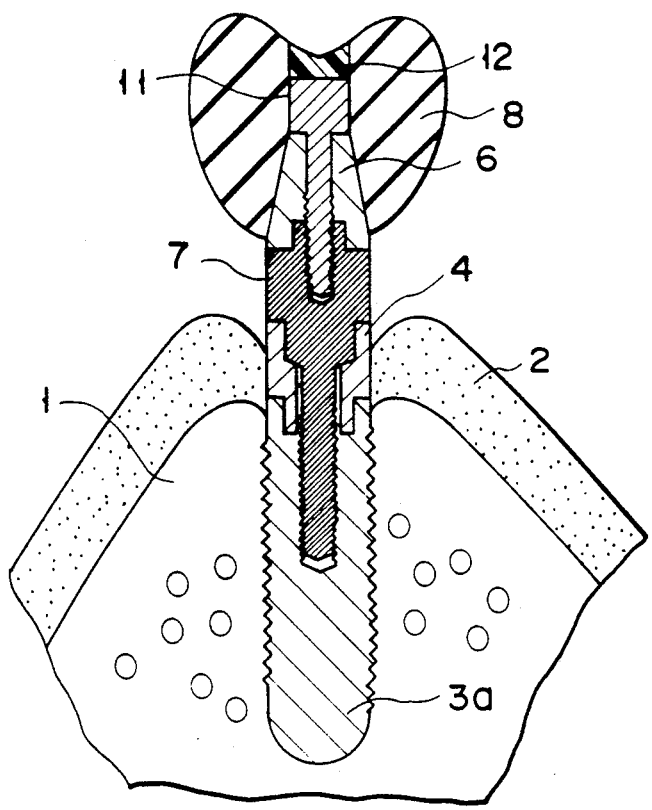
FIG. 3 shows a buccolingual sectional view of the dental implant of the first embodiment according to the present invention which has been implanted in a target position.

The super elastic materials employed in the present invention are those in which strain recovers almost zero value upon removing the load, even after the strain exceeding an elastic limit is imposed. An example of such a super elastic material is a shape memory alloy.

The curve of stress vs. strain of an alloy having the shape memory effect is as shown in FIG. 1 at a temperature slightly higher than its inverse transformation temperature. The curve of stress vs. strain represents super elasticity which is one of the properties of the shape memory alloy. Thus, the strain recovers almost zero value upon removing the loaded stress, even after a stress which gives several % elongation to in excess of the elastic limit is imposed. On the other hand, in cases of usual metals, as is evident from the curve of stress vs. strain shown in FIG. 2, the strain exceeding the elastic limit does not recover zero value even when the loaded stress is removed, resulting in residual strain.

In the present invention, a shape memory alloy having an inverse transformation temperature slightly lower than the oral cavity temperature can be employed as the super elastic material. The temperature slightly lower than the oral cavity temperature herein means a temperature not higher than 35° C., preferably from 20° to 25° C. Examples of such shape memory alloys are listed below.

* Ni-Ti alloy: (e.g. 48-52 at % Ni, Ti balance)
* Ni-Ti-Cu alloy: (e.g. 49.5 at % Ti, 40.5 at % Ni, 10 at % Cu)
* Ni-Al alloy: (e.g. 36-38 at % Al, Ni balance)
* Ni-Ti-Co alloy: (e.g. 31-33 at % Ni, 5-15 at % Co, 3.5-5 at % Ti, Fe balance)
* Cu-Zn alloy: (e.g. 38.5-41.5 wt% Zn, Cu balance)
* Ti-Mo-Al alloy: (e.g. 80-87 at % Ti, 13-15 at % Mo, 0-5 at % Al)

Among these, Ni-Ti alloy is especially preferred.

As a polymeric material in the present invention, polymers having great vibration damping rate and non-toxicity, for example, polyoxymethylene, nylon 6, nylon 66, nylon 46, teflon, silicone and the like may be employed.

In the present invention, the shock absorbing member made of a super elastic material provided between the implant body and the post core exhibits the following functions.

In the cases where the stress upon occlusion is within the range of the elastic deformation of the super elastic material employed, sufficient occlusal force can be obtained since the upper structure (artificial tooth) is steadily supported by the implant body through the super elastic material member.

On the other hand, in case that the stress upon occlusion exceeds the elastic limit of the super elastic material, the super elastic material greatly deforms as the super elastic deformation, while absorbing the occlusal force, resulting in prevention of increased stress. Therefore, by designing the yield stress of the super elastic material so that the stress being imposed on the jaw bone around the implant body does not exceed the breaking strength of the jaw bone, it is possible to prevent the damage of the jaw bone due to the excessive occlusal force.

Even after receiving the stress exceeding the elastic limit from a great occlusal force, the super elastic material recovers the original shape when such the great occlusal force is removed. Accordingly, deviation of the occlusal position does not occur, which deviation is usual with a case of using an ordinary metal due to remaining of permanent residual strain.

The shape memory alloy employed as the super elastic material also has an effect to damp the impact since the alloy has an excellent anti-vibration property due to the presence of martensite twin.

In addition, durability may be enhanced compared with a shock absorbing member made of polymeric materials by using a shape memory alloy so designed that the inverse transformation temperature is lower than the oral cavity temperature.

Furthermore, in case of employing a shock absorbing member made of polymeric materials in addition to the member made of shape memory alloy, the polymeric material member also has an effect of damping the vibration so as to absorb the impact which may damage the jaw bone, thus enabling to protect the jaw bone.

Moreover, the shape memory alloy used as super elastic materials has an excellent anti-vibration effect due to the presence of the martensite twin as described above, and the shock absorbing member made of the shape memory alloy can achieve extremely enhanced impact-damping effect due to the multiplier effect obtained from combination with the polymeric material member.

In addition, in case of the combination of the super elastic material and the polymeric material, occlusal stress of usual strength is sustained by almost only the super elastic member. Therefore, the polymeric material member is free from the great stress which causes deterioration or destruction, in contrast with the conventional shock absorbing system composed of only polymeric material such as polyoxymethylene. As a result, it is not required to replace the polymeric material member with a new one.

The present invention is further described according to the examples.

FIG. 3 shows a buccolingual sectional view of the dental implant according to the first example of the present invention which is embedded in a target position. In this figure, jaw bone (alveolar bone) 1 and gingiva 2 are indicated. In jaw bone 1, artificial root 3a, 4 made of titanium is embedded. The artificial root consists of implant body 3a and gingiva-penetrating member 4. The part of implant body 3a deeper than 2 mm under the bone surface is provided on the surface in contact with jaw bone 1 with a coating layer mainly consisting of beta-TCP. The coating layer serves, by means of facilitating synostosis of implant body 3a embedded in jaw bone 1 at an early stage, to secure implant body 3a tightly to jaw bone 1 without the need of the help of interstitial fibrous tissue. In a practical surgery, implant body 3a is first embedded in jaw bone 1, and then a screw hole provided in the top of implant body 3a is closed with a Teflon lid, which is then covered with gingiva 2 entirely while taking care not to damage periosteum.

Once implant body 3a is secured to jaw bone 1 via synostosis, the gingiva is excised to remove the Teflon lid. Subsequently, titanium gingiva-penetrating member 4 in a cylindrical form is engaged with or adhered to the implant body 3a, thereby forming artificial root. Then super elastic member 7 made of an alloy of 48-52 at % Ni/52-48 at % Ti designed so as to have a inverse transformation temperature from 20° to 25° C. is screwed downward into artificial root 3a, 4 to ensure the fixation.

After post 6 which has been bonded to artificial tooth 8 made of a resin is secured to the top of Ni-Ti super elastic member 7 using artificial tooth fixing screw 11, the space above the fixing screw 11 is filled with resin filler 12.

By means of the structure wherein super elastic member 7 is provided between artificial root 3a, 4 and post 6 as in the example mentioned above, damage of alveolar bone 1 can be prevented even when an excessive occlusal force is applied. Thus, upon receiving excessive occlusal force, super elastic member 7 greatly deforms exceeding the elastic limit to absorb the occlusal force. Accordingly, no stress which may damage alveolar bone 1 is given to the alveolar bone. Therefore, a stable bone fixation of the dental implant over a long period is achieved. In addition, super elastic member 7 made of Ni-Ti alloy does not have to be replaced for a long period since it is hard to be degraded or damaged when compared with conventional shock absorbing member made of polymeric materials such as POM.

Figure 4:
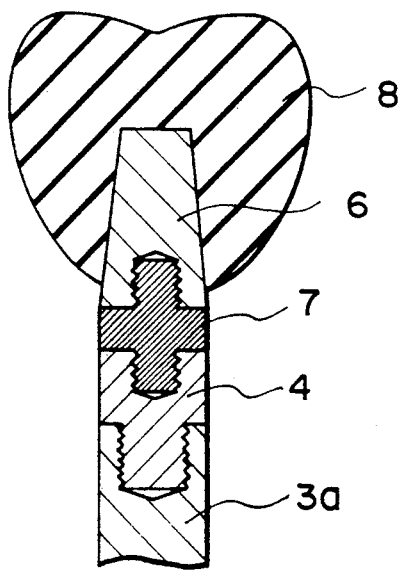
FIGS. 4 and 5 show sectional views representing modifications of the embodiment shown in FIG. 1.
Figure 5:
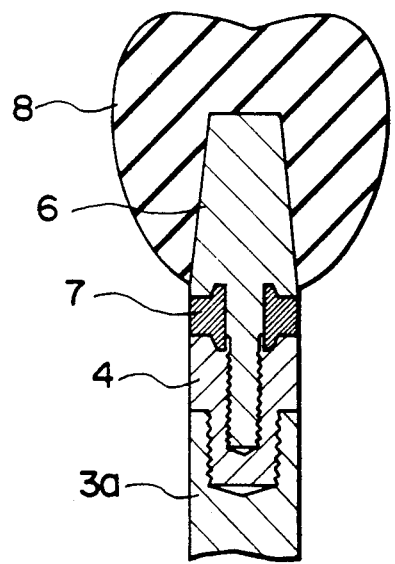

The forms of implant body 3a, gingiva-penetrating member 4, super elastic member 7 and post 6 as well as the methods of securing them are not limited to those described above. For example, as shown in FIG. 4, each of implant body 3a, gingiva-penetrating member 4, super elastic member 7 and post 6 may be secured by a screw. Also as shown in FIG. 5, super elastic member 7 in a form of a disk with a through hole in its center may be secured to gingiva-penetrating member 4 via a screw provided in post 6.

Although the example described above employs titanium artificial root 3a, 4 roots made from titanium alloy or ceramic materials such as zirconium oxide may also be used.

Figure 6:
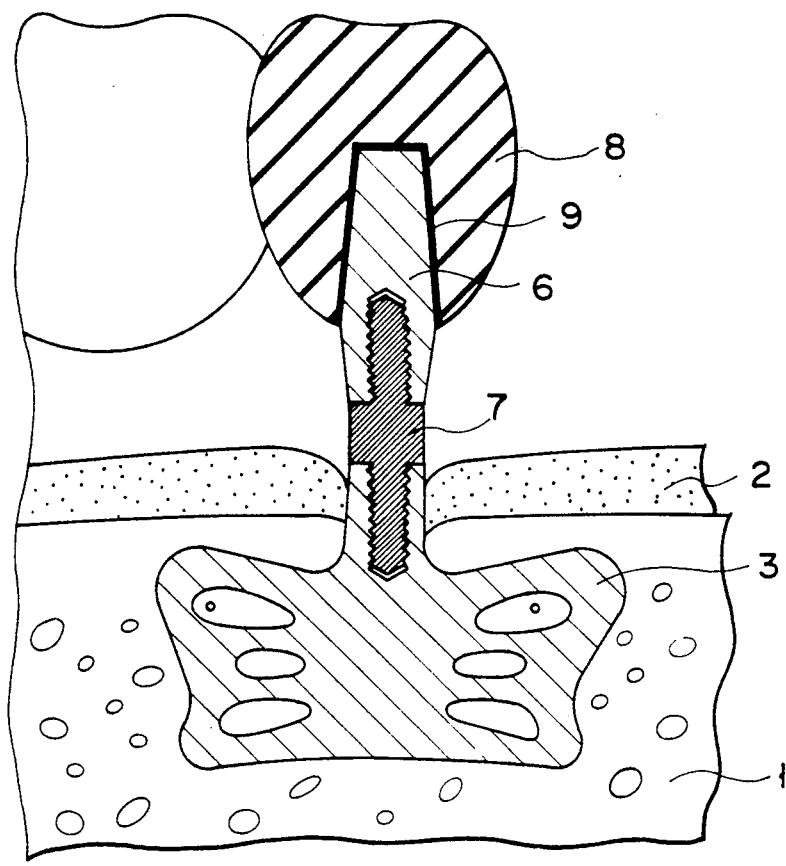
FIG. 6 shows a buccolingual sectional view of the dental implant of the second embodiment of the present invention which has been implanted in a target position.

FIG. 6 shows a buccolingual sectional view of the dental implant according to the second embodiment of the present invention which is implanted in a target position. In this embodiment, blade type artificial root 3 is employed. In this figure, the same numerals as used in the example shown in FIG. 1 are employed to designate the same members.

Artificial root 3 of a blade type is so embedded in alveolar bone 1 that the position of the screw hole used to form the upper structure might be higher than gingiva 2. After artificial root 3 is tightly secured in alveolar bone 1, the upper structure is formed. Thus, Ti-Ni super elastic member 7 is screwed into artificial root 3, and post 6 is fixed on super elastic member 7. Then, bridge artificial tooth 8 is bound to post 6 and adjacent teeth using dental cement 9.

Also in the embodiment of blade type implant as mentioned above, by means of the structure wherein super elastic member 7 is provided between artificial root 3 and post 6, an effect similar to that in the embodiment shown in FIG. 3 can be obtained. Thus, in cases of excessive occlusal force applied, super elastic member 7 deforms exceeding the elastic limit to absorb the occlusal force, thereby maintaining a function of the dental implant over a long period without damage of the alveolar bone. In addition, there is obtained another advantage in replacement of Ti-Ni super elastic member is not required over a prolonged period since it has less tendency to be degraded or damaged.

Figure 7:
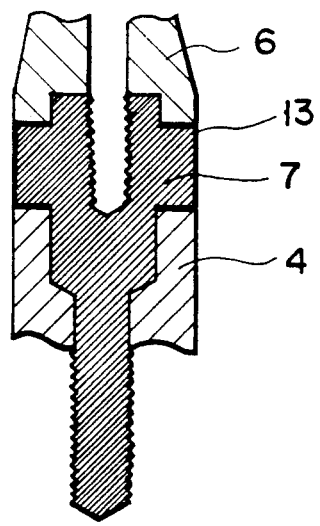
FIG. 7 shows a sectional view of essential portions of the dental implant of the third embodiment of the present invention.

FIG. 7 shows a sectional view of an essential part of the dental implant according to the third embodiment of the present invention. In this embodiment the surface of Ni-Ti super elastic member 7 is covered with pure titanium thin layer 13 at the area exposed in the oral cavity and at a part of the area in contact with post 6. Ni-Ti super elastic member 7 is so designed that its inverse transformation temperature is slightly higher than the oral temperature. Pure titanium thin layer 13 is so designed that it is thin enough not to affect the stress-strain characteristics of super elastic member 7. Another construction is similar to that of the embodiment shown in FIG. 3.

Also in the third embodiment, by means of super elastic member 7, the alveolar bone is protected from damage even when an excessive occlusal force is applied. In addition, release of metal ions from Ni-Ti alloy is reduced to a low level because the surface of the super elastic member 7 at a part exposed in oral cavity is covered with pure titanium thin layer 13, resulting in an enhanced safety. Furthermore, pure titanium thin layer 13 is prevented from falling off, since the top and the bottom of pure titanium thin layer 13 are fixed between post 6 and gingiva-penetrating member 4, respectively.

Figure 8:
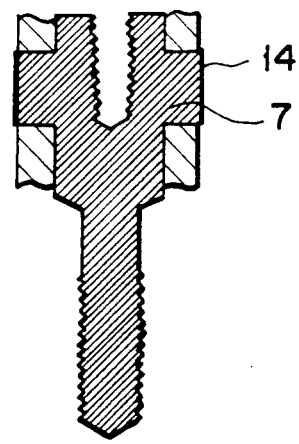
FIG. 8 shows a sectional view of essential portions of the dental implant of the fourth embodiment of present invention.

FIG. 8 shows a sectional view of the dental implant according to the fourth embodiment of the present invention. In this embodiment, the surface of Ni-Ti super elastic member 7 is coated with Teflon coating 14 at the area exposed in the oral cavity. Other structure is similar to that of the embodiment shown in FIG. 3.

According to this embodiment, it is possible to reduce the metal release from super elastic member 7 to a further lower level while maintaining the characteristics of super elastic member 7, resulting in a further increased safety. Similar effects can be obtained by using other biologically non-toxic polymeric materials other than Teflon for the coating 14, such as polyethylene and nylon.

Similar effects can also be obtained by applying analogue means to the dental implant shown in FIG. 4 to FIG. 6, although pure titanium thin layer 13 and Teflon coating 14 are applied to the dental implant of FIG. 3 in the third and fourth embodiment, respectively.

Figure 9:
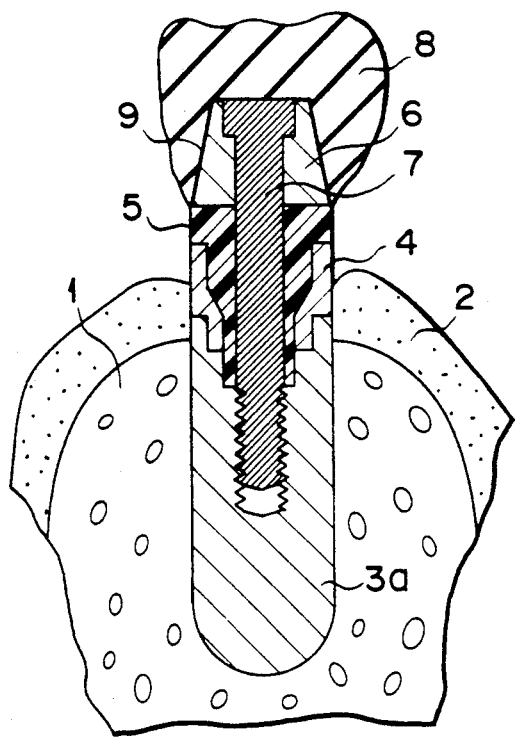
FIG. 9 shows a sectional view of the essential portions of the dental implant of the fifth embodiment of the present invention.

FIG. 9 shows a buccolingual sectional view of the fifth embodiment of the present invention. In jaw bone 1, titanium implant body 3a is embedded. The part of the surface of implant body 3a which is deeper than 2 mm under the bone surface and is in contact with jaw bone 1 is provided with a coating layer mainly consisting of beta-TCP, which serves, by means of facilitating synostosis of implant body 3a at an early stage, to secure implant body 3 tightly to jaw bone 1 without the need of the help of interstitial fibrous tissue. In a practical surgery, titanium implant body 3a is first implanted in jaw bone 1, and then a screw hole provided in the top of titanium implant body 3a for the purpose of constructing the upper structure is closed with a Teflon lid, which is then covered with gingiva 2 entirely while taking care not to damage periosteum. Thereafter, the site of the surgery should be allowed to stand still until titanium implant body 3a is secured to jaw bone 1 by means of synostosis.

Once implant body 3a is secured to jaw bone 1 via synostosis, the gingiva is excised to remove the Teflon lid, and titanium gingiva-penetrating member 4 in a cylindrical form is then fixed into or adhered to titanium implant body 3a. Then Ni-Ti alloy super elastic member 7 which is designed to have an inverse transformation temperature slightly lower than the oral cavity temperature, for example, 20° to 25° C., is screwed into titanium implant body 3a downward via nylon 66 polymeric member 5 and titanium post 6 to secure the nylon 66 polymeric member 5 and titanium post 6.

In this embodiment, nylon 66 polymeric member 5 has at least two parts which have outer diameters equal to the outer and inner diameters of gingiva-penetrating member 4 respectively. The part having the diameter equal to the inner diameter of gingiva-penetrating member 4 penetrates while being in contact with the inner surface of gingiva-penetrating member, and the bottom thereof reaches implant body 3a. Along with the axis of nylon 66 polymeric member 5, a hole to be penetrated by super elastic member 7 is provided.

Finally artificial tooth 8 is bound by dental cement (binding layer 9) to post 6 which was constructed on the top of titanium implant body 3a as mentioned above.

By means of the structure wherein super elastic member 7 and polymeric member 5 are provided between titanium implant body 3a and post 6 to which artificial tooth 8 is bound as in the embodiment mentioned above, super elastic member 5 greatly changes in shape with by exceeding the elastic limit upon an excessive occlusal force applied, thereby absorbing the occlusal force being. Accordingly, no stress which may damage jaw bone 1 is given to the jaw bone. Therefore, a stable bone fixation of the dental implant over a long period is achieved. In addition, though super elastic member 7 made from Ni-Ti alloy shows several % of strain when loaded with stress, the strain recovers zero value completely once the stress is removed. Therefore, the deviation of the occlusal position, which is frequently observed with standard metals such as titanium or titanium alloy, can be prevented.

Furthermore, by combining Ni-Ti alloy super elastic member 7 and nylon 66 polymeric member 5, standard occlusal stress is able to be supported by almost only Ni-Ti alloy super elastic member 5, while relatively less significant stress, which may cause degradation or damage of the polymeric member, is applied to nylon 66 polymeric member 5 when compared to a conventional art device in which only polymeric member 5, made from, for example, polyoxymethylene, serves as a stress absorbing mechanism. Therefore, there is no need to replace polymeric member 5 of the present invention over a long period.

Figure 10:
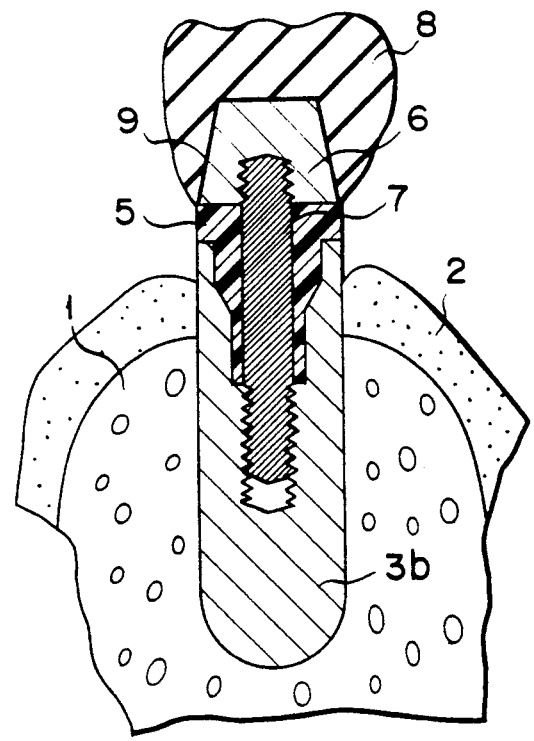
FIG. 10 shows a sectional view representing a modification of the embodiment shown in FIG. 9.

The shape and securing method for the stress absorbing system consisting of super elastic member 7 and polymeric member 5 is not specifically limited to those mentioned above. For example, as shown in FIG. 10, post 6 is screwed into super elastic member 7, and super elastic member 7 is then screwed downward from the top of polymeric member 5 through a through hole formed in polymeric material into artificial root 3b which is integrated with the gingiva-penetrating member.

Figure 11:
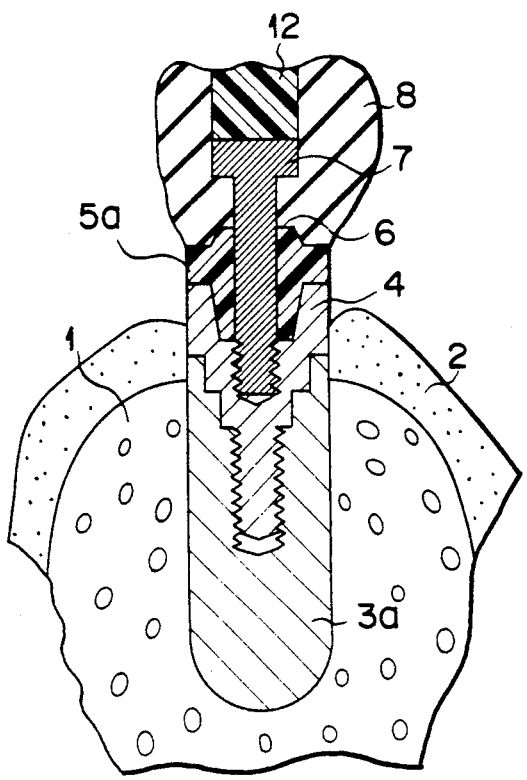
FIG. 11 shows a sectional view representing another modification of the embodiment shown in FIG. 9.
Figure 12:
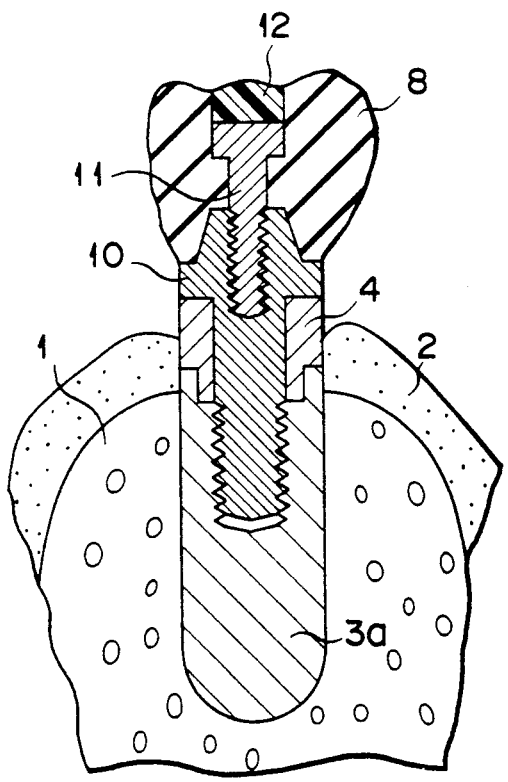
FIGS. 12 to 14 show sectional views of conventional dental implants.
Figure 13:
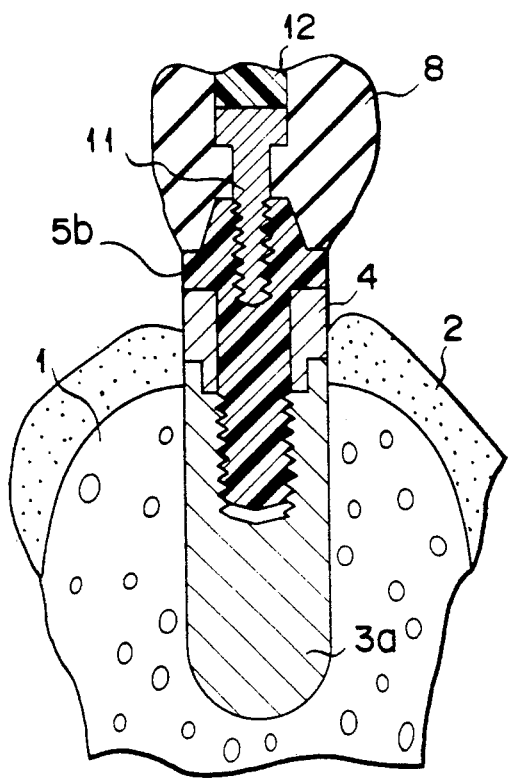
Figure 14:
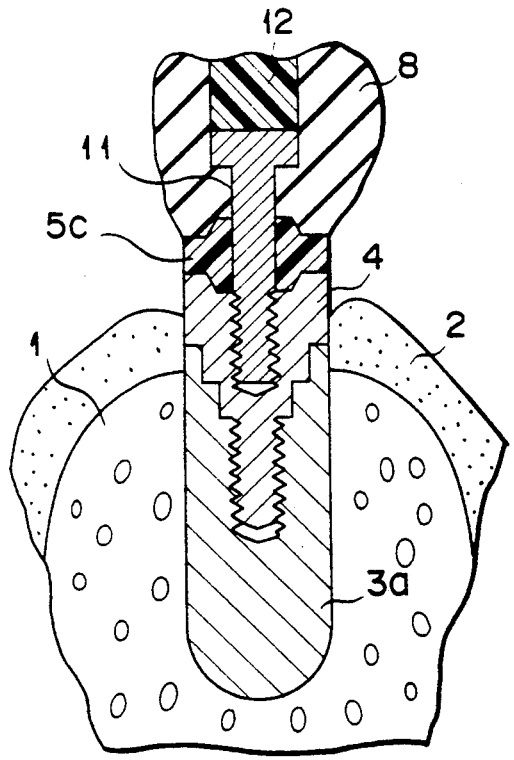

Also as shown in FIG. 11, gingiva-penetrating member 4 having a screw hole on the top thereof for securing artificial tooth securing screw (super elastic member) 7 is screwed into implant body 3a. On gingiva-penetrating member 4, polymeric member 5a having a hole along with the axis to be penetrated by super elastic member 7 and trapezoid post 6, as well as artificial tooth 8 having the lower shape to allow close contact with post 6 of polymeric member 5a are mounted. Then artificial tooth securing screw 7 is screwed into gingiva-penetrating member 4 in such a manner that artificial tooth 8 and polymeric member 5a are sandwiched. Finally filler 12 is applied to artificial tooth to fill the space above artificial tooth securing screw 7.

As detailed above, the dental implant according to the present invention not only provides a necessary and sufficient occlusal force but also prevents damage of the jaw bone in cases of excessive occlusal force applied, without the need of replacement of a shock absorber.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A dental implant comprising an artificial root adapted to be embedded in a jaw bone and a post to which an artificial tooth is attached, wherein said artificial root is formed of an elastic material having a high rigidity and wherein a stress absorbing member formed of a super elastic material is provided in at least a portion of a connection portion between said artificial root and said post.

2. A dental implant according to claim 1, wherein the artificial root comprises an implant body and a gingiva-penetrating member.

3. A dental implant according to claim 1, wherein the stress absorbing member comprises a super elastic member and a polymeric member at least a part of which is in contact with the super elastic member.

4. A dental implant according to claim 3, wherein the polymeric material is formed into a trapezoid post.

5. A dental implant according to claim 2, wherein the stress absorbing member comprises a super elastic member and a polymeric member, and the stress absorbing member is provided in such a manner that at least a part of the super elastic member is in direct contact with both the implant body and the post, and that the polymeric member is in contact with at least a part of the side surface of the super elastic member.

6. A dental implant according to claim 1, wherein the super elastic material comprises a shape memory alloy having an inverse transformation temperature lower than the oral cavity temperature.

7. A dental implant according to claim 6, wherein the inverse transformation temperature of the shape memory alloy is 35° C. or lower.

8. A dental implant according to claim 7, wherein the inverse transformation temperature of the shape memory alloy is between 20° and 25° C.

9. A dental implant according to claim 6, wherein the shape memory alloy is Ni-Ti alloy.

10. A dental implant according to claim 9, wherein at least portions of the Ni-Ti shape memory alloy exposed to an oral cavity are covered with a biologically less-hazardous material than said Ni-Ti alloy.

11. A dental implant according to claim 9, wherein the biologically less-hazardous material is selected from the group consisting of a biological less-hazardous metal and a biological less-hazardous polymeric material.

12. A dental implant according to claim 11, wherein said biologically less-hazardous metal is a titanium thin film.

13. A dental implant according to claim 11, wherein said biologically less-hazardous polymeric material is selected from the group consisting of Teflon, polyethylene and nylon.

14. A dental implant according to claim 1, wherein said connection portion is provided separately from said artificial root and said post.

15. A dental implant according to claim 1, wherein said super elastic material is provided only in said connection portion between said artificial root and said post.

* * * * *